(12) United States Patent
Cassol et al.

(10) Patent No.: US 7,825,259 B2
(45) Date of Patent: Nov. 2, 2010

(54) METHOD OF PREPARATION OF HALOGEN-FREE IONIC LIQUIDS AND IONIC LIQUIDS PREPARED IN THIS MANNER

(75) Inventors: Cláudia Cristiana Cassol, Porto Alegre (BR); Bauer Costa Ferrera, Porto Alegre (BR); Gunter Ebeling, Porto Alegre (BR); Jairton Dupont, Porto Alegre (BR)

(73) Assignee: Petroleo Brasileiro S.A. - Petrobras, Rio De Janeiro (BR)

( * ) Notice: Subject to any disclaimer, the term of this patent is extended or adjusted under 35 U.S.C. 154(b) by 17 days.

(21) Appl. No.: 11/790,352

(22) Filed: Apr. 25, 2007

(65) Prior Publication Data

US 2008/0045723 A1    Feb. 21, 2008

(30) Foreign Application Priority Data

Aug. 15, 2006    (BR) .................................. 0603210

(51) Int. Cl.
C07D 233/54    (2006.01)
C07F 1/00    (2006.01)
(52) U.S. Cl. .................................... 548/335.1; 548/402
(58) Field of Classification Search ................. 548/402, 548/335.1
See application file for complete search history.

(56) References Cited

FOREIGN PATENT DOCUMENTS

WO    WO 01/40146    6/2001
WO    WO 03/074494    9/2003

OTHER PUBLICATIONS

Holbrey et al; "Efficient, halide free synthesis of new, low cost ionic liquids: 1,3-dialyklomidazolium salts containing ethyl- and ethyl-sulfate anions"; Green Chemistry; vol. 4; 2002; pp. 407-413.*
Dupont et al; "Ionic Liquid (Molten Salt) Phase Organometallic Catalysis"; Chemical Reviews; vol. 102, No. 10; 2002; pp. 3667-3691.
Wasserscheid et al; "Ionic Liquids—New "Solutions" for Transition Metal Catalysis"; Angew. Chem. Int. Ed.; vol. 39; 2000; pp. 3772-3789.
Welton; "Room-Temperature Ionic Liquids. Solvents for Synthesis and Catalysis"; Chemical Reviews; vol. 99, No. 8; 1999; pp. 2071-2083.
Wilkes et al; "Dialkylimidazolium Chloroaluminate Melts: A New Class of Room-Temperature Ionic Liquids for Electrochemistry, Spectroscopy, and Synthesis"; Inorganic Chemistry; vol. 21, No. 3; 1982; pp. 1263-1264.
Wilkes et al; "Air and Water Stable 1-Ethyl-3-Methylimidazolium Based Ionic Liquids"; J. Chem. Soc., Chem. Commun.; 1992; p. 965-967.
Suarez et al; "The Use of New Ionic Liquids in Two-Phase Catalytic Hydrogenation Reaction by Rhodium Complexes"; Polyhedron; vol. 15, No. 7; 1996; pp. 1217-1219.
Dupont et al; "Preparation of 1-Butyl-3-Methylimidazolium-Based Room Temperature Ionic Liquids"; Organic Synthesis; vol. 79; 2002; pp. 236-247.
C. Villangran et al; "Quantification of Halide in Ionic Liquids Using Ion Chromatography"; Analytical Chemistry; vol. 76, No. 7; 2004; pp. 2118-2123.
Sweeny et al; "Cyclic voltammetric study of the catalytic behavior of nickel(I) salen electrogenerated at a glassy carbon electrode in an ionic liquid (1-butyl-3-methylimidazolium tetrafluoroborate, BMIM ⁻BF₄")"; Electrochemistry Communications 3; 2001; pp. 712-715.
Gallo et al; "How does the presence of impurities change the performance of catalytic systems in ionic liquids? A case study: the Michael addition of acetylacetone to methyl vinyl ketone"; J. Chem. Soc., Dalton Trans.; 2002; pp. 4339-4342.
Seddon et al; "Influence of chloride, water, and organic solvents on the physical properties of ionic liquids"; Pure and Applied Chemistry; vol. 72. No. 12; 2000; pp. 2275-2287.
Holbrey et al; "Efficient, halide free synthesis of new, low cost ionic liquids: 1,3-dialyklomidazolium salts containing methyl- and ethyl-sulfate anions"; Green Chemistry; vol. 4; 2002; pp. 407-413.
Jodry et al; "New chiral imidazolium ionic liquids: 3D-network of hydrogen bonding"; Tetrahedron Letters 45; 2004; pp. 4429-4431.
De Souza et al; "Alternative Synthesis of a Dialkylimidazolium Tetrafluoroborate Ionic Liquid Mixture and its Use in Poly(acrylonitrile-butadiene) Hydrogenation"; Adv, Synth. Catal.; vol. 344; No. 2; 2002; pp. 153-155.

* cited by examiner

*Primary Examiner*—Joseph K. McKane
*Assistant Examiner*—Janet L Coppins
(74) *Attorney, Agent, or Firm*—Nixon & Vanderhye P.C.

(57) ABSTRACT

The reaction of N-alkylimidazol with alkyl sulfonates, at room temperature, favors the production of 1,3-dialkylimidazolium alkane-sulfonates as crystalline solids at high yields. The alkane-sulfonate anions may be easily substituted by a series of other anions [$BF_4$, $PF_6$, $PF_3(CF_2CF_3)_3$, $CF_3SO_3$ and $(CF_3SO_2)_2N$] through simple anion, salt, or acid reactions in water at room temperature. The extraction with dichloromethane, filtration, and evaporation of the solvent, allows the production of the desired ionic liquids at a yield of 80-95%. The purity of these ionic liquids (in some cases >99.4%) is performed using the intensity of $^{13}C$ satellite signals from the magnetic resonance spectrums of the N-methyl imidazolium group as an internal standard.

1 Claim, 1 Drawing Sheet

METHOD OF PREPARATION OF HALOGEN-FREE IONIC LIQUIDS AND IONIC LIQUIDS PREPARED IN THIS MANNER

CROSS REFERENCE TO RELATED APPLICATION

This application is based upon, claims the benefit of, priority of, and incorporates by reference, the contents of Brazilian Patent Application No. PI 0603210-9 filed Aug. 15, 2006.

FIELD OF THE INVENTION

The present invention relates to the field of ionic liquids, more in particular to a method of preparing halogen-free ionic liquids produced from the cation 1,3-dialkylimidazolium.

BACKGROUND OF THE INVENTION

Ionic liquids, also know as molten salts, are made up of salts derived from tetra alkyl ammonium or phosphonium or, more frequently, made up of heteroaromatic cations associated with anions, such as, for example, $BF_4$, $PF_6$, $CF_3SO_3$, $(CF_3SO_2)_2N$, $CF_3CO_2$ (P. Wasserscheid, T, Welton; Ionic Liquids in Synthesis, VCH-Wiley, Weinheim, 2002; J. Dupont; R. F. de Souza, P. A. Z. Suarez; Chem. Rev.; 2002, 102, 3667; P. Wasserscheid, W. Keim; Angew. Chem. Int. Ed.; 2000, 39, 3773; T. Welton; Chem. Rev.; 1999, 99, 2071), and in a general way these ionic liquids are mainly used industrially as reagents or solvents.

The most researched and used ionic liquids are those based on the 1,3-dialkylimidazolium cation, and its physical and chemical properties qualify it as a "green" solvent in many processes, such as, for example, processes of extraction/separation, synthesis, catalysis, electrochemical.

The use of ionic liquids as a "green" reaction medium is primordially described as substituent for conventional mediums in chemical processes.

With growing concerns about the environment, the use of ionic liquids as a reaction medium can provide a way to minimize the production of wastes. In ionic liquids it is possible not only to efficiently promote reactions, but also to contribute significantly to minimize solvent loss.

There are applications in which the ionic liquids play the role of lubricating agent between metallic parts that undergo a high level of mechanical wear. Again, the absence of free halogens that may form cells in the presence of small amounts of water or polar compounds is very important. It is known today, that in industry, minimal amounts (mg/L) of halogens compounds in pyrolysis furnaces feedstocks, for example, can lead to planned maintenance down time due to corrosion in the pipes or even disintegration of refractories.

Therefore, the use of ionic liquids in addition to providing ecological benefits, also translates into economic advantages.

The Article by J. S. Wilkes et al (Inorg. Chem.; 1982, 21, 1263) presents a synthesis of 1,3-dialkylimidazolium chlorides that makes it possible to introduce similar or different alkyl groups. Mixtures of these chlorides with anhydrous aluminum chloride, in various proportions, provide ionic liquids.

Another Article by J. S. Wilkes et al (J. Chem. Soc., Chem. Commun.; 1992, 965), explains a method for exchanging a chloride salt of 1,3-dialkylimidazolium ion with various anions, such as $BF_4$ and $CH_3CO_2$, by reacting imidazolium chlorides with a silver salt containing the desirable anion.

The Article by J. Dupont et al (Polyhedron; 1996, 15, 1217) describes a new method for this reaction, with a sodium salt used as the desired counter ion and acetone as solvent.

The Article by J. Dupont et al (Org. Synth.; 2002, 79, 236) presents a detailed optimization of the experimental procedure of replacing a halogen anion of the 1,3-dialkylimidazolium salts with $BF_4$, $PF_6$ or $CF_3SO_3$.

The patent belonging to P. Wasserscheid et al (EP 03/02127, dated Sep. 12, 2003) describes the synthesis, through metathesis reactions, of some ionic liquids with a general formula of [cation]+.[$ROSO_3$]—. Thus, for example, the heating under vacuum of a mixture of 1-butyl-3-methylimidazolium with pyridinium diethylene glycol-monomethyl-ether-sulfate provides, after removing the pyridinium chloride by sublimation, the ionic liquid, butylmethylimidazolium diethylene glycol-monomethyl-ether-sulfate. In another procedure, a 1-butyl-3-methylimidazolium chloride interacts with ammonium diethylene glycol-monomethyl-ether-sulfate in $CH_2Cl_2$, the ammonium chloride precipitate was filtered and the filtrate was concentrated, yielding the ionic liquid, 1-butyl-3-methylimidazolium diethylene glycol-monomethyl-ether-sulfate.

The halogen metathesis method is well established nowadays; it allows synthetized, in a convenient manner, a wide range of ionic liquids derived from the cation 1,3-dialkylimidazolium. The residual contaminant is usually chloride that may be detected by testing with $AgNO_3$ (1.4 mg/L limit), ionic chromatography (under 8 mg/L, in accordance with C. Villangran et al; Anal. Chem.; 2004, in press), or by cyclic voltammetry (ppb, according to B. K. Sweeny et al; Electrochem. Commun.; 2001, 3, 712). The water content may be determined by Karl-Fischer titration or by cyclic voltammetry (V. Gallo et al; J. Chem. Soc., Dalton Trans.; 2002, 4339). The determination of the presence and quantity of these impurities is essential in many applications, because the physico-chemical properties of the ionic liquids may vary significantly, depending on the water or halogen content (K. R. Seddon et al; Pure Appl. Chem.; 2000, 72, 2275).

Some processes for obtaining halogen free ionic liquids are described in the literature.

In K. R. Seddon et al's patent (WO 01/40146, dated Jul. 6, 2001) a process is described where the salts of 1,3-dialkylimidazoliums are prepared by alkylation of 1-alkylimidazolium with trifluoroethyl acetate or with butyl methanesulfonate, under reflux and purification by vacuum and heat, followed by a metathesis reaction of the anions with acids, such as, for example, $HBF_4$ or $HPF_6$.

In the Article by J. D. Holbrey et al (Green Chem.; 2002, 4, 407), 1-alkylimidazoliums are alkylated with dimethyl sulfate or with diethyl sulfate and, consequently, the anion ($CH_3OSO_3$ or $CH_3CH_2OSO_3$) is exchanged for $BF_4$, $PF_6$ or $CF_3SO_3$.

The Article by K. Mikami et al (Tetrahedron Lett; 2004, 45, 4429) describes obtaining a salt of 1,3-dialkylimidazolium chiral through alkylation of 1-methylimidazolium with the triflic ester derived from (S)-ethyl-lactate (Diagram 1).

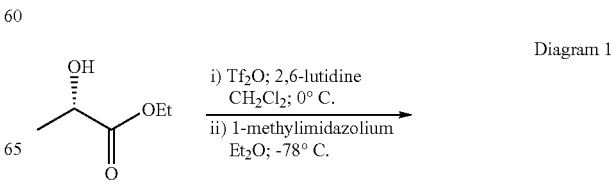

Diagram 1

-continued

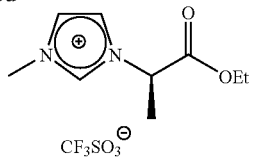

The salt shown above is a solid one, however, metathesis with $PF_6$ allows a derivative of an ionic liquid to be obtained.

The Article by J. Dupont et al (Adv. Synth. Catal.; 2002, 344, 153), proposes a reaction where five components (glyoxal, formaldehyde, two different amines and an acid) are condensed to 1,3-dialkylimidazolium salts.

Undoubtedly, the derivatives of the cation 1,3-dialkylimidazolium associated with several anions are among the most investigated types of ionic liquids.

Very probably this is due to their facility to be synthesized, they are stable, and their physico-chemical properties can be fine-tuned by simply selecting the N-alkyl substituents and/or anions.

The great majority of these ionic liquids are usually prepared through the simple N-alkylation of N-alkylimidazol, generally using alkyl halogens as alkylation agents, followed by the association of metal halides or anion metathesis.

The anion metathesis procedures generate a great variety of ionic liquids based on 1,3-dialkylimidazolium of good quality.

Determining the purity of these ionic liquids is not a simple task. The principal contaminant is usually a residual halogen from the alkylation of imidazolium that may be detected by testing with $AgNO_3$ (1.4 mg/L limit), ionic chromatography (under 8 mg/L), or by cyclic voltammetry (ppb). The water content may be determined by Karl-Fischer titration or by cyclic voltammetry. The determination of the presence and the quantity of these impurities is essential in many applications, such as in catalysis and spectroscopic investigation, once the physico-chemical properties of the ionic liquids may vary significantly, depending on the water and/or halogen content.

At all events, as mention before, according to J. Dupont, et al, ionic liquids 1,3-dialkylimidazolium halogen free may be prepared from the reaction of five components (glyoxal, formaldehyde, two different amines and acids) and those containing alkyl sulfate or trifluoromethane sulfonate anions by the simple alkylation of 1-alkylimidazolium with the corresponding dialkyl sulfate or an alkyl trifluoromethane sulfonate ester, respectively.

Among the advantages of ionic liquids based on 1,3-dialkylimidazolium cations we can point out the following:
  They are non-volatile, with no measurable vapor pressure;
  They are usually liquids within a wide range of temperatures (close to room temperature) and their viscosity is sufficiently low (<800 cP to 20° C.);
  They have thermal and electrochemical stability more suitable than the usual solvents;
  They dissolve a wide range of organic and inorganic compounds, on which their solubility may be adjusted by the choice of alkyl groups linked to the imidazole ring or by the nature of the anion;
  They are typically non-coordinate solvents;
  They are easily prepared from commercial reagents and through classic synthetic procedures.
Similar procedures to obtain ionic liquids which use alkyl sulfonates and alkyl phosphate as alkylation agents have been patented. However, in almost all the work carried out in this area it has been observed that there is a strong participation of halogenated materials, and no matter what future application in industrial units industries might be for these ionic liquids, it will be very important to guarantee the stability of these materials and preferably the absence of these anions in their free form.

Currently, ionic liquids such as [butylmethylimidazolium] $PF_6$, [butylmethylimidazolium] $BF_4$ e [butylmethylimidazolium] $(CF_3SO_2)_2N$ are commercially available, but with relatively high levels of chloride contaminants.

However, it is surprising that up to now there is no quick method available to prepare and to determine the purity of 1,3-dialkylimidazolium cation halogen free associated with the most popular and the most used anions such as $PF_6$, $BF_4$ and $(CF_3SO_2)_2N$.

It is clear that there is a need for simpler and more practical methods to prepare halogen free ionic liquids and also there is a need for a quicker and more direct methodology to determine their purities.

SUMMARY OF THE INVENTION

In the present invention a simple and quick method to prepare halogen free ionic liquids, derived from the 1-alkyl-$(C_1-C_{18})$, 3-alkyl-$(C_1-C_{18})$-imidazolium cation, associated with the anions $PF_6$, $BF_4$, $(CF_2CF_3)_3PF_3$, $CF_3SO_3$ and $(CF_3SO_2)_2N$ is presented, using a process with only two stages that may be sequential or not, at temperature close to room temperature and whose purity (>99%) may be determined using the $^{13}C$ satellites of the hydrogen nuclear magnetic resonance spectrum of the N-alkyl group as an internal standard, particularly the N-methyl group.

DETAILED DESCRIPTION OF THE INVENTION

Figure 1:
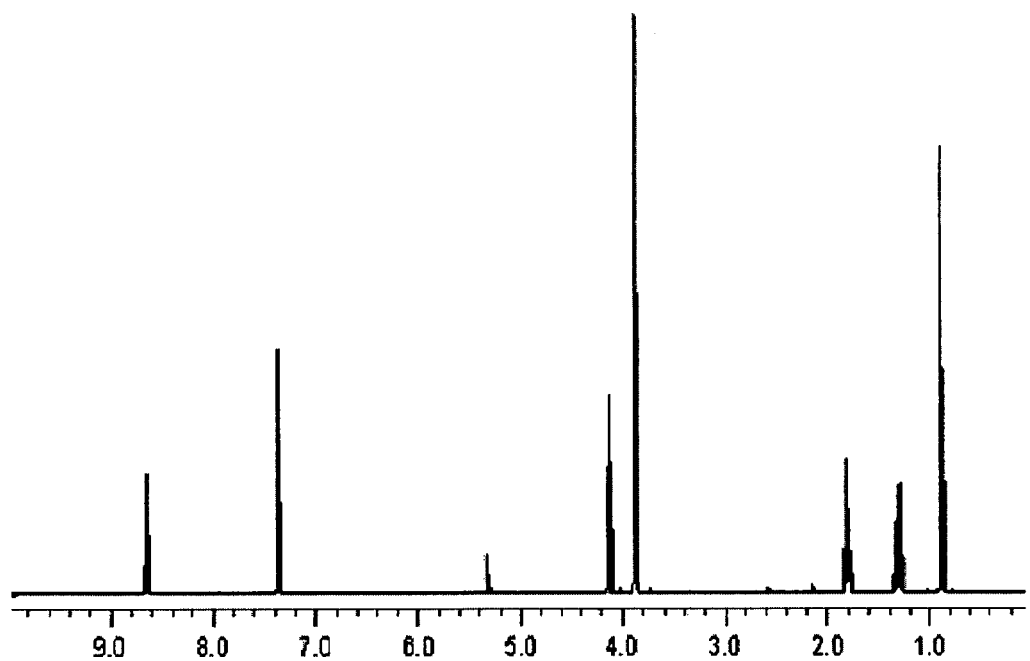
FIG. 1 shows the hydrogen nuclear magnetic resonance spectrum (500 MHz, 25° C.) of 1-butyl-3-methylimidazolium tetrafluoroborate ($BMI.BF_4$) in $CD_2C_{12}$.
Figure 2:
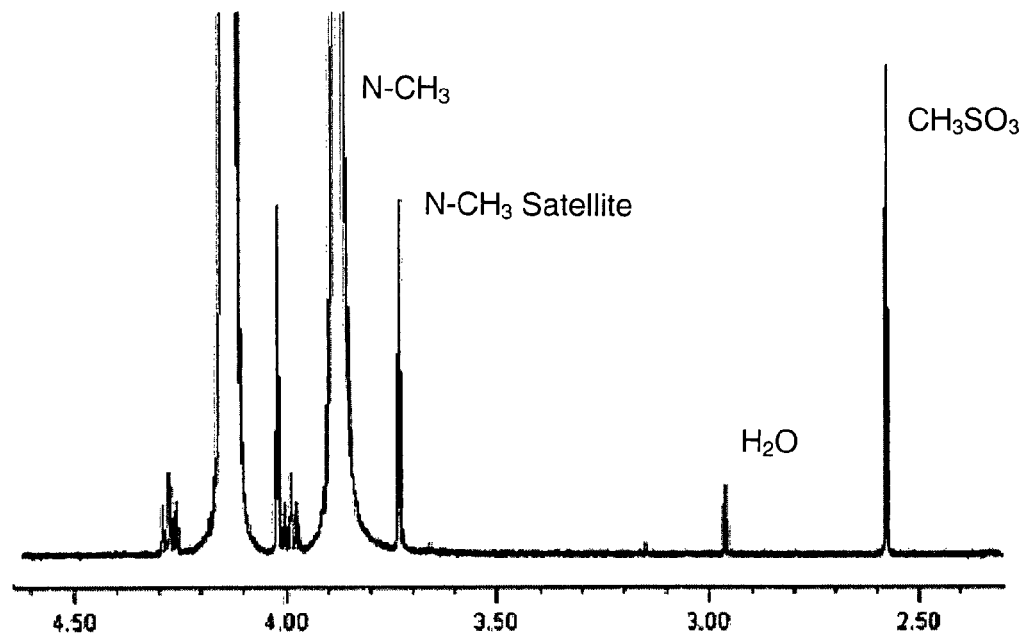
FIG. 2 shows the expansion between 2.50 and 4.50 mg/L, showing the signals relating to the $^{13}C$ satellites and the signals relating to water and to $CH_3SO_3$ group in the start-up compound (1-butyl-3-methylimidazolium methanesulfonate). (Relative intensities: a $^{13}C$ satellite=9.25, of the methanesulfonate anion=23.44 and of water=1.528).

The present invention refers to a method to prepare ionic liquids, derived from the 1-alkyl-$(C_1-C_{18})$, 3-alkyl-$(C_1C_{18})$-imidazolium cation free of halogen, using a two stage process that may be sequential, or not, and that includes:
  i) Alkylation of 1-alkyl $(C_1-C_{18})$-imidazoliums with alkyl $(C_1-C_{18})$ alkane $(C_1-C_{18})$ sulfonates or with alkyl $(C_1-C_{18})$ trifluoromethanesulfonate.
  ii) Metathesis reaction, in a water solution, of the alkyl $(C_1-C_{18})$ alkane $(C_1-C_{18})$ sulfonates with alkaline metal salts containing the anions $PF_6$, $BF_4$, $CF_3SO_3$, $(CF_3SO_2)_2N$, $(CF_3CF_2)_3PF_3$, and similar.

The determination of the purity of the ionic liquids is performed using the intensity of $^{13}C$ satellite signals from the hydrogen nuclear magnetic resonance spectrums in the N-methyl group as an internal standard.

Preferred Methods of Implementation

Herein after, we presented the preferred forms of implementation of the present invention, through some 1-alkylimidazolium alkylation reactions:

I) 1-alkyl ($C_1$-$C_{18}$)-imidazoliums were alkylated with alkyl ($C_1$-$C_{18}$) alkane ($C_1$-$C_{18}$) sulfonates by mixing the reagents in acetonitrile, chloridated solvents, or preferably, in the absences of solvents. In this procedure, the temperature of reaction must be kept between 0 and 80° C., preferably between 15 and 30° C., keeping the reagents in contact in a period of 6 to 96 hours. The alkyl groups of sulfonic esters that are linked to the oxygen atom may be primary or secondary, while the alkyl groups linked to the sulfur atom may be primary, secondary, or tertiary.

II) 1-alkyl ($C_1$-$C_{18}$)-imidazoliums were alkylated with alkyl ($C_1$-$C_{18}$) trifluoromethane sulfonates by mixing the reagents in chlorates solvents, preferably, in dichloromethane. In this procedure, the temperature of reaction must be kept between −10 and 25° C., preferably between 0 and 5° C., keeping the reagents in contact in a period of 1 to 4 hours. The alkyl groups of the trifluoromethane sulfonate esters that are linked to the oxygen atom may also be primary or secondary.

III) The alkylation of 1-alkyl ($C_1$-$C_{18}$)-imidazoliums was also performed with alkyl ($C_1$-$C_{18}$) trifluoromethane sulfonates generated in situ, through primary or secondary reactions of alcoholysis ($C_1$-$C_{18}$) with anhydrous sulfonic trifluoromethane, in the presence of 1-alkyl ($C_1$-$C_{18}$) imidazoliums and subsequent treatment of the reaction mixture with sodium carbonate.

EXAMPLES

Example 1

1-butyl-3-methyl imidazolium methane-sulfonate (BMI.$CH_3SO_3$)

Butyl methanesulfonate (45.60 g; 300 mmol) was mixed with 1-methyl imidazolium (24.60 g; 300 mmol) and the reaction mixture was allowed to stand at room temperature (25° C.) for 48 hours. After this period of time, an identical volume of acetone and one 1-butyl-3-methylimidazolium methanesulfonate crystal were added, in order to induce the crystallization of the product. The mixture was kept in the refrigerator overnight. A yellow, supernatant solution was decanted from the almost colorless crystals and the crystallization process was again repeated. After drying under vacuum, colorless BMI.$CH_3SO_3$ crystals were obtained (59.70 g; 85% yield); the melting point was 77.2° C., RMN—$^1$H (CDCl$_3$) δ:

9.67 ($^1$H, s, C—H imidazolium);
7.47 (1H, t, J=1.8 Hz, C—H imidazolium);
7.36 (1H, t, J=1.8 Hz, C—H imidazolium);
4.11 (2H, t, J=7.2 Hz, NCH$_2$);
3.89 (3H, s, NCH$_3$);
2.59 (3H, s, CH$_3$SO$_3$);
1.72 (2H, quintet, J=7.2 Hz, CH$_2$);
1.20 (2H, sextet, J=7.2 Hz, CH$_2$);
0.79 (3H, t, J=7.2 Hz, CH$_3$);
RMN—$^{13}$C (CDCl$_3$) δ:
137.4; 123.5 and 121.8 (C—H imidazolium);
49.2 (NCH$_2$);
39.4 (CH$_3$SO$_3$);
35.9 (NCH$_3$);
31.7 and 19.0 (CH$_2$);
13.0 (CH$_3$).

Example 2

1-Butyl-3-methylimidazolium 2-butanesulfonate

Butyl 2-butanesulfonate (24.88 g; 154 mmol) was mixed with 1-methyl imidazolium (12.30 g; 150 mmol) and the reaction mixture was allowed to stand at room temperature (25° C.) for 60 hours. After this period of time, the yellow reaction mixture became solidified. The crystalline mass was crushed, washed two times with ethyl acetate and dried under vacuum, which produced colorless crystals of 1-butyl-3-methyl imidazolium 2-butanesulfonate (33.10 g, 80% yield), melting point 76.1° C. RMN—1H (CDCl$_3$) δ: 9.80 (1H, s, C—H imidazolium); 7.53 (₁H, t, J=1.5 Hz, C—H imidazolium); 7.39 (1H, t, J=1.5 Hz, C—H imidazolium); 4.15 (2H, t, J=7.5 Hz, NCH$_2$); 3.92 (3H, s, NCH$_3$); 2.72-2.60 (1H, m, CH$_3$CH$_2$CH(CH$_3$)SO$_3$); 2.20 5-2.05 (1H, m, CH$_3$CH$_2$CH(CH$_3$)SO$_3$); 1.87 (2H, quintet, J=7.5 Hz, CH$_2$); 1.54-1.30 (3H, m, CH$_3$CH$_2$CH(CH$_3$)SO$_3$ and CH$_2$); 1.32 (3H, d, J=6.8 Hz, CH$_3$CH$_2$CH(CH$_3$)SO$_3$); 0.99 (3H, t, J=7.5 Hz, CH$_3$CH$_2$CH(CH$_3$)SO$_3$); 0.94 (3H, t, J=7.5 Hz, CH$_3$). RMN—$^{13}$C (CDCl$_3$) δ: 137.6; 123.6 and 121.8 (C—H imidazolium); 56.7 (CH$_3$CH$_2$CH(CH$_3$)SO$_3$); 49.2 (NCH$_2$); 36.0 (NCH$_3$); 31.8; 24.6 and 19.0 (CH$_2$); 14.5; 13.1 and 11.5 (CH$_3$).

Example 3

1,3-dimethyl imidazolium methanesulfonate

Methyl methanesulfonate (5.50 g; 50 mmol) was mixed with 1-methyl imidazolium (4.10 g; 50 mmol) and the reaction mixture was allowed to stand at room temperature (25° C.) for 60 hours. After this period of time, the yellow reaction mixture became solidified. The crystalline mass was crushed, washed two times with ethyl acetate and dried under vacuum, which produced colorless crystals of 1,3-dimethyl imidazolium methanesulfonate (8.16 g, 85% yield), melting point 93.1° C. RMN—$^1$H (CDCl$_3$) δ: 9.81 (1H, s, C—H imidazolium); 7.43 (2H, s, C—H imidazolium); 4.02 (6H, s, NCH$_3$); 2.79 (3H, s, CH$_3$SO$_3$). RMN—$^{13}$C (CDCl$_3$) δ: 138.5 and 123.3 (C—H imidazolium); 39.4 (CH$_3$SO$_3$); 36.3 (NCH$_3$).

Example 4

1-butyl-3-methyl imidazolium trifluoromethane-sulfonate (BMI.$CF_3SO_3$)

4.1—First Variant:

Methyl trifluoromethanesulfonate (C. D. Beard et al; J. Org. Chem; 1973, 38, 3673) (4.26 g; 26.0 mmol) was added drop by drop, under stirring, into a cold solution (0° C.) of 2-butyl-imidazolium (3.10 g; 25.0 mmol) in 20 mL of dichloromethane. The resulting mixture was stirred for 30 minutes. 1 drop of water was added and shaken for one more hour. The reaction mixture was treated with anhydrous sodium carbonate and the resulting suspension was shaken for 30 minutes. Filtering followed by evaporation of the solvent produced the desired BMI.$CF_3SO_3$, a light yellow liquid (6.84 g; 95% yield). RMN—$^1$H (CDCl$_3$) δ: 9.03 (1H, s, C—H imidazolium); 7.48 (1H, s, C—H imidazolium); 7.47 (1H, s, C—H imidazolium); 5 4.21 (2H, t, J=7.3 Hz, NCH$_2$); 3.97 (3H, s, NCH$_3$); 1.87 (2H, quintet, J=7.3 Hz, CH$_2$); 1.36 (2H, sextet, J=7.3 Hz, CH$_2$); 0.91 (3H, t, J=7.3 Hz, CH$_3$).

4.2—Second Variant:

1-Methyl-imidazolium (2.74 g; 33.3 mmol) was mixed together with n-butanol (2.47 g; 33.3 mmol) in 40 mL of dichloromethane and, under stirring and cooling in an ice bath, anhydrous sulfonic trifluoromethane (9.40 g; 33.3 mmol) was added drop by drop. After finishing the addition to the mixture, it was stirred for 1 hour at room temperature, to which a saturated aqueous solution of sodium carbonate (3.54 g; 33.3 mmol) was added. The solution was stirred for 30 minutes at room temperature. The phases were separated, with an organic dry phase that uses anhydrous sodium carbonate. The solvent was evaporated under vacuum and gently heated (50° C.), producing the desired $BMI.CF_3SO_3$ (7.19 g; 75% yield), identical to the material obtained in experiment 1.2.4.1.

Example 5

Anion Metathesis Reactions 5.1—1-butyl-3-methylimidazolium tetrafluoroborate ($BMI.BF_4$).

A mixture formed by 1,3-dimethyl imidazolium methanesulfonate ($BMI.CH_3SO_3$) (10.6 g; 45.0 mmol), sodium tetrafluoroborate (6.00 g; 54.5 mmol) and water (5.4 mL) was stirred at room temperature for 30 minutes. The resulting mixture, made up of two phases, was extracted with dichloromethane (3×15 mL). The combined organic extract was dried with anhydrous sodium carbonate and the solvent was evaporated under vacuum and heated (80° C.), which produced the desired $BMI.BF_4$ ionic liquid. (9.35 g; 92% yield).

5.2—1-butyl-3-methylimidazolium hexafluorophosphate ($BMI.BF_4$).

A mixture formed by 1,3-dimethyl imidazolium methanesulfonate ($BMI.CH_3SO_3$) (5.80 g; 24.6 mmol), sodium hexafluorophosphate (5.00 g; 29.8 mmol) and water (5.0 mL) was stirred at room temperature for 30 minutes. The resulting mixture, made up by two phases, was extracted with dichloromethane (3×10 mL). The combined organic extract was washed with water (2×20 mL) and dried with anhydrous sodium carbonate. The solvent was evaporated under vacuum and heated (80° C.), which produced the desired ionic liquid $BMI.PF_6$ (6.64 g; 95% yield).

5.3—1-Butyl-3-methylimidazolium N-trifluoro-sulfonamidate [$BMI.(CF_3SO_2)_2N$].

A mixture formed by 1,3-dimethyl imidazolium methanesulfonate ($BMI.CH_3SO_3$) (4.26 g; 18.2 mmol), lithium N-trifluoro sulfonimidate (5.47 g; 19.1 mmol) and water (10.0 mL) was stirred at room temperature for 45 minutes. The resulting mixture, made up by two phases, was extracted with dichloromethane (3×15 mL). The combined organic extract was washed with water (1×20 mL) and dried with anhydrous sodium carbonate. The solvent was evaporated under vacuum and heated (80° C.), which produced the desired ionic liquid $BMI.(CF_3SO_2)_2N$ (7.33 g. 96% yield).

Example 6

Determination of the Purity of Ionic Liquid

The purity of the ionic liquids may be conveniently determined by the hydrogen nuclear magnetic resonance using the signals from the $^{13}C$ satellites (1.11% natural abundance) where the intensity of each $^{13}C$ satellite represents 0.56%. For example, the ionic liquids derived from the 1-butyl-3-methylimidazolium cation obtained through the metathesis reaction of alkylsulfonates with the alkaline salts of tetrafluoroborate, hexafluorophosphate, N-trifluor-sulfonimidate, etc., the residual sulfonate alkanes are quantified using the intensity of the $^{13}C$ satellite signals from the N-methyl radical of the imidazolium nucleus of the product as a standard (the intensity of each $^{13}C$ represents 0.56%), in the hydrogen magnetic resonance spectrum (FIG. 1). The residual amount of water may also be quantified in this manner.

Notwithstanding the fact that this invention has been presented in accordance with its preferred implementations, those well acquainted with the technology will be able to see that variations and modifications may be made to the present invention, without distracting from its spirit and scope, which are defined by the following claims.

The invention claimed is:

1. A method for preparing halogen-free ionic liquids, the method comprising the following steps:
   i) reacting 1-alkyl ($C_1$-$C_{18}$)-imidazolium with alkyl ($C_1$-$C_{18}$) alkane ($C_1$-$C_{18}$) sulfonates or with alkyl ($C_1$-$C_{18}$) trifluoromethanesulfonate, wherein the 1-alkyl ($C_1$-$C_{18}$)-imidazolium is alkylated;
   ii) reacting, in a metathesis reaction in an aqueous solution, alkyl ($C_1$-$C_{18}$) alkane ($C_1$-$C_{18}$) sulfonates with alkaline metal salts containing $BF_4$, $CF_3SO_3$, $(CF_3SO_2)_2N$, or $(CF_3CF_2)_3PF_3$; and
   iii) obtaining a halogen-free ionic liquid from steps (i) and (ii).

* * * * *